United States Patent [19]

Sasson

[11] Patent Number: 5,138,107
[45] Date of Patent: Aug. 11, 1992

[54] PHASE TRANSFER CATALYZED HALOGENATION OF CARBON ACIDS

[75] Inventor: Yoel Sasson, Jerusalem, Israel

[73] Assignee: E. I. Du Pont de Nemours and Company, Wilmington, Del.

[21] Appl. No.: 730,183

[22] Filed: Jul. 12, 1991

[51] Int. Cl.$^5$ .................. C07C 17/00; C07C 17/02; C07C 69/60; C07C 3/00
[52] U.S. Cl. .................. 570/200; 554/153; 558/460; 560/174; 564/204; 564/209; 568/316; 568/409; 568/437; 568/460; 570/101; 570/190; 570/206; 570/216; 570/261
[58] Field of Search .................. 558/460; 560/174; 564/204, 209; 568/316, 409, 419, 436, 437, 459, 490, 495, 946; 570/200, 216, 261, 190, 206; 260/408

[56] References Cited

U.S. PATENT DOCUMENTS 4,740,624  4/1988  Kohler et al. .................. 568/316
4,806,280  2/1989  Mignani et al. .................. 260/408

OTHER PUBLICATIONS

C. Y. Meyers et al., New Synthesis and Reactions of Organic Compounds: Reactions with Carbon Tetrachloride and Other Perhalomethanes in Powdered Potassium Hydroxide-t-Butyl Alcohol. pp. 197-278.
M. Makosza et al., ROCZ Chem. 43, pp. 671-676.
A. Jonczyk et al., J. Org. Chem., 44, pp. 1192-1194.
S. E. Lauritzen et al., Acta Chem Scan, B 35, 1981, pp. 263-268.
Y. Hori et al., Rikogakubu Shoho, 6, pp. 19-22.
Y. Hori et al., Chem. Lett., 1978, pp. 73-76.
W. P. Reeves et al., "The Phase Transfer Catalyzed Preparation of 2-Methyl-2-Tricholormethyl-3-Phenyloxirane" Synth Comm., 13(11), 945-950 (1983).
C. Y. Meyers et al. "Facile and Selective Chlorination-Cleavage of Some Cyclanones and Cyclanols with the $CCl_4$-KOH-t-BuOH Reagent. In Situ Conversion of Estrones and Estradiols into Dichlorodoisynolic Acids" I. Org. Chem., 43, 1985-1990.
C. R. Hauser et al., "Reactions of Alkali Diphenylmethides with Certain Polyhalides. Displacement on Halogen or Hydrogen", I. Org. Chem., 26, pp. 2627-2629 (1961).

Primary Examiner—Werren B. Lone

[57] ABSTRACT

A process is disclosed for chlorinating, brominating and/or iodinating an organic substrate containing both a single acidic hydrogen atom and at least one electron withdrawing group attached to the same carbon atom. The process replaces the single acidic hydrogen with chlorine, bromine and/or iodine and involves reacting the substrate in solution with a halogenating agent (e.g., a perhalomethane wherein the halogen substituents are I, Br and/or Cl, a trihaloacetic acid ester wherein the halogen substituents are Br and/or Cl, or a perfluoroalkyl halide wherein the halide is I, Br and/or Cl) in the presence of (i) a phase transfer catalyst of the formula $R^1R^2R^3R^4LJ$ where L is selected from the group consisting of phosphorus and nitrogen, where J is an inorganic anion other than fluoride, and where $R^1$, $R^2$, $R^3$ and $R^4$ are independently chosen from the froup consisting of hydrocarbyl radicals containing from 1 to about 20 carbon atoms and (ii) a mild inorganic base which is insoluble in the reaction medium.

24 Claims, No Drawings

PHASE TRANSFER CATALYZED HALOGENATION OF CARBON ACIDS

FIELD OF THE INVENTION

This invention relates to the halogenation of compounds containing an acidic proton on a carbon atom, and more particularly providing catalysts for such halogenations.

BACKGROUND OF THE INVENTION

Under strongly basic conditions, tetrahalomethanes are known to generate chloronium or bromonium ions, which can be used to halogenate carbanions. The halogenation of ketones, sulfones, alcohols, and acidic hydrocarbons with perhalomethanes, e.g., $CCl_4$, $CBr_4$, $CBrCl_3$, $CCl_2Br_2$, in tert-butyl alcohol using powdered potassium hydroxide has been reviewed by C.Y. Meyers, et al., Catalysis in Organic Synthesis 1977, G.V. Smith, ed., pp. 197-278.

Halogenation reactions are also known to take place under conditions of phase transfer catalysis with a stoichiometric amount of aqueous sodium hydroxide as the base and benzyltriethylammonium chloride (TEBA) as catalyst (M. Majiszam et al., Rocz Chem. 1969, 43, 671-676; A. Jonczyk, et al., J. Org. Chem., 44, 1192-1194 (1979); S.E. Lauritzen, et al., Acta Chem. Scand. B 35, 1981, 263-268).

Active hydrogen compounds can also be chlorinated using 1,8-diazabicyclo[5.4.0]undecene-7 (i.e., "DBU") and $CCl_4$ (Y. Hori, et al., Rikogakubu Shuho (Saga Daigaku), 1978, 6, 19-22); and brominated using $DBU/BrCCl_3$ (Y. Hori, et al., Chem. Lett., 1978, 73-76).

U.S. Pat. No. 4,806,280, Mignani, et al., Rhone-Poulenc Sante (1989), discloses a process for preparing α-chlorinated unsaturated compounds with respect to two electron-attracting groups in the β-position. The preferred halogenating agents are molecular chlorine, sulfuryl chloride, N-chlorosuccinimide, and hexachloroethane.

SUMMARY OF THE INVENTION

This invention provides a process for halogenating an organic substrate containing both a single acidic proton and at least one electron withdrawing group attached to the same carbon atom, using a quaternary ammonium or phosphonium salt (e.g., tetra-n-butylammonium bromide) as a catalyst, to replace the proton (i.e., the hydrogen atom) with a halogen atom selected from the group consisting of chlorine, bromine and iodine. The process is reversible and comprises the step of reacting the substrate in solution with a halogenating agent in the presence of (i) a phase transfer catalyst of the formula $R^1R^2R^3R^4LJ$ where L is selected from the group consisting of phosphorus and nitrogen, where J is an inorganic anion other than fluoride, and where $R^1$, $R^2$, $R^3$ and $R^4$ are independently chosen from the group consisting of hydrocarbyl radicals containing from 1 to about 20 carbon atoms and (ii) a mild inorganic base which is insoluble in the reaction medium. Halogenating agents for this process include perhalomethanes wherein the halogen substituents are I, Br and/or Cl, trihaloacetic acid esters wherein the halogen substituents are Br and/or Cl, and perfluoroalkyl halides wherein the halide is I, Br and/or Cl.

It is an object of this invention to provide a process wherein the reaction takes place under conditions in which starting materials or products containing labile moieties such as ester groups and halogen groups, can be used or can be produced without being destroyed by hydrolytic processes that occur under strongly basic conditions.

It is another object of this invention to provide a process wherein exotic reagents, such as DBU, are not necessary.

Further objects, features and advantages of the invention will be apparent from the following detailed description.

DETAILED DESCRIPTION OF THE INVENTION

This invention provides a process of halogenating certain organic substrates by replacing an acidic hydrogen atom on a carbon atom with an atom of chlorine, bromine, or iodine. The process involves a liquid-solid reaction of the substrate in solution using a halogenating agent, a solid base and a catalytic amount of a quaternary ammonium salt or quaternary phosphonium salt.

The catalyst may be any compound of formula $R^1R^2R^3R^4LJ$, where L is selected from the group consisting of phosphorus and nitrogen, where J is an inorganic anion other than fluoride, and where $R^1$, $R^2$, $R^3$, and $R^4$ are independently chosen from the group consisting of hydrocarbyl radicals containing from 1 to about 20 carbon atoms. J may suitably be selected from the group consisting of $Cl^-$, $Br^-$, $I^-$, $HSO_4^-$ and $NO_3^-$. $R^1$, $R^2$, $R^3$ and $R^4$ may be aliphatic (linear, branched or alicyclic), aromatic or mixed aliphatic-aromatic groups. Aliphatic groups containing from 1 to about 10 carbon atoms are preferred. Preferred aliphatic groups include alkyl groups such as n-butyl, n-hexyl, and n-octyl with n-butyl most preferred. Preferred aliphatic-aromatic groups contain from 7 to about 20 carbon atoms. For desirable reaction rates, the quaternary ammonium or quaternary phosphonium catalyst should generally be soluble in the reaction mixture. The catalyst is usually added at the start of the reaction along with the substrate, the base and the halogenating agent.

Preferred catalysts include inorganic salts (preferably $Cl^-$, $Br^-$ or $HSO_4^-$ salts, most preferably $Cl^-$ salts) of tetraethylammonium, tetraethyl phosphonium, tetra-n-butylammonium, tetra-n-hexylammonium, tetra-n-hexylphosphonium, tetra-n-octylammonium, tetraphenylphosphonium, and tri-capryl-methylammonium, with tetra-n-butylammonium and tri-capryl-methylammonium being particularly preferred. Quaternary ammonium salts and quaternary phosphonium salts are relatively common, commercially available reagents.

The substrate halogenated in the process of this invention must have a carbon atom bearing both a single acidic proton and at least one electron withdrawing group. Examples of substrates which can be halogenated in accordance with this invention include monosubstituted acetylene derivatives of the formula $R^5—C\equiv C—H$. $R^5—C\equiv$ is an electron withdrawing group. $R^5$ is a hydrocarbyl group, preferably containing between 1 and about 10 carbon atoms. $R^5$ may be an aliphatic (including linear, branched or alicyclic), aromatic or mixed aliphatic-aromatic group, and may be unsubstituted or substituted with a group inert under reaction conditions (e.g., a halogen). Examples of suitable aliphatic groups include linear or branched alkyl groups such as n-butyl, n-hexyl, n-octyl, isobutyl, and trifluoromethyl. Examples of suitable aromatic groups include $-C_6H_5$ and $-C_6H_4Br$. Examples of suitable aliphatic-aromatic groups include $-CH_2C_6H_5$. Substituted and unsubstituted aromatic groups (e.g., phenyl or substituted phenyl) are preferred.

Examples of substrates that can be halogenated in accordance with this invention also include compounds of the formula, HCXYZ, wherein X is an electron withdrawing group. The electron withdrawing group of X may be for example a nitrile group (i.e., —CN), an aldehyde group (i.e., —CHO), a ketone group of the formula $-C(=O)-R^6$, or an ester group of the formula $-C(=O)-OR^6$, where $R^6$ is a hydrocarbyl group, preferably containing between 1 and about 10 carbon atoms. $R^6$ may be an aliphatic (linear, branched or alicyclic) aromatic or mixed aliphatic-aromatic group and may be unsubstituted or substituted with a group which is inert under reaction conditions (e.g., a halogen). Examples of suitable X groups include —COOCH$_3$, —COOC$_2$H$_5$, —COCH$_3$ and —CN. Y may be selected from the same groups as X (i.e., it may be an electron withdrawing group) or it may be an aromatic group, preferably containing from 6 to about 20 carbon atoms (e.g., —C$_6$H$_5$) which is unsubstituted or substituted with a group which is inert under reaction conditions (e.g., a halogen). Examples of suitable Y groups include —COOCH$_3$, —COOC$_2$H$_5$, and —COCH$_3$. Z may be selected from the same groups as Y (i.e, it may be an electron withdrawing group or an unsubstituted or inert group-substituted aromatic group), or it may be an linear or branched, saturated or unsaturated alkyl group, preferably containing between 1 and about 10 carbon atoms which is unsubstituted or substituted with a group which is inert under reaction conditions (e.g., a halogen). Examples of suitable Z groups include —CH$_3$, —C$_2$H$_5$ and —C$_6$H$_5$.

Examples of substrates that can be halogenated in accordance with this invention also include trihalomethanes wherein each of the three halogen groups is selected from the group consisting of Cl, Br, I and F. The three halogens of the trihalomethane function together as electron withdrawing groups such that the single hydrogen of the trihalomethane is acidic. Examples of trihalomehtanes include CHCl$_3$, CHBr$_3$, CHI$_3$, CHF$_3$, CHCl$_2$Br, CHCl$_2$I, CHCl$_2$F, CHBr$_2$Cl, CHBr$_2$I and CHBr$_2$F.

The substrate should be at least partially soluble in the reaction medium. The reaction medium should not interfere with the course of the reaction. The reaction medium can comprise, for example, toluene, tetrahydrofuran, or benzene. In many preferred embodiments, such as where the halogenating agent is a liquid at ambient temperature, the reaction medium consists essentially of the halogenating agent.

The halogenating agents used for this process are selected from the group consisting of perhalomethanes wherein the halogen substituents are I, Br and/or Cl (e.g., CCl$_4$, CBr$_4$, CBrCl$_3$ and/or CCl$_2$Br$_2$); trihaloacetic acid esters wherein the halogen substituents are Br and/or Cl (e.g., Cl$_3$CC(=O)OCH$_3$); and perfluoroalkyl halides, preferably containing from 1 to 10 carbon atoms wherein the halide is I, Br and/or Cl (e.g., perfluoro-n-hexyl iodide). The reaction is reversible and the halogenated substrate can itself serve as a donor for other halogenations (e.g., for halogenating bromoform). Accordingly, it is preferred to use a molar excess (e.g., at least about 10 percent excess) of halogenating agent (relative to the substrate).

A preferred halogenating agent for chlorination is CCl$_4$. A preferred halogenating agent for bromination is CBrCl$_3$. Preferred halogenating agents for iodination include perfluoroalkyl iodides. When the halogenating agent is not being used as the reaction medium, it is preferably soluble in the reaction medium.

The halogenation reaction can be run at a temperature of from about 0° C. to 150° C. The preferred temperature range is from about 30° to 100° C., and the most preferred range is from about 60° to 80° C.

One of the primary advantages of this process is that it need not be run under strongly alkaline conditions. Thus the potential for hydrolysis of esters and other such materials that are labile in strong base, as well as hydrolysis of the halogenated product is reduced. Instead, a mild inorganic base is used. The base may be selected from among carbonates and fluorides that are insoluble in the reaction medium. In general, preferred bases include Na$_2$CO$_3$, K$_2$CO$_3$, Cs$_2$CO$_3$, NaHCO$_3$ and KF. For the mono-substituted acetylene derivatives discussed above (i.e., R$^5$—C≡C—H) Cs$_2$CO$_3$ is the preferred base.

The time of reaction typically ranges from about 30 minutes to about 24 hours and depends upon such factors as the nature and concentration of the reactants and the catalyst.

One method of practicing this invention involves stirring the substrate and halogenating agent at about room temperature (i.e., about 24° C.) with sufficient base and catalyst to achieve halogenation within about 2 hours.

Practice of the invention will become further apparent from the following non-limiting examples:

EXAMPLE 1

Diethyl ethylmalonate (1.88 g, 10 mmol), 1.38 g (10 mmol) of potassium carbonate, 0.1 g of tetra-n-butylammonium chloride hydrate, and 5 mL of carbon tetrachloride were mixed at 70° C. for 3 h. Gas chromatographic analysis of the mixture showed complete conversion of the diethyl ethylmalonate to yield 2.13 g of diethyl α-chloro-α-ethylmalonate (96% yield).

EXAMPLE 2

Dimethyl methylmalonate (1.46 g, 10 mmol), 1.0 g (12 mmol) sodium bicarbonate, 0.1 g of tetra-n-butylammonium chloride hydrate, and 5 mL of carbon tetrachloride were mixed at 70° C. for 4 h. Complete conversion of dimethyl methylmalonate was determined by gas chromatography. Yield of dimethyl α-chloro-α-methylmalonate was 1.71 g (95%).

EXAMPLE 3

Dimethyl methylmalonate (1.46 g, 10 mmol), 1.0 g (17.2 mmol) of potassium fluoride, 0.1 g of tetra-n-butylammonium chloride hydrate, and 5 mL of carbon tetrachloride were mixed at 70° C. for 4 h. Complete conversion of dimethyl methylmalonate was determined by gas chromatography. Yield of dimethyl α-chloro-α-methylmalonate was 1.76 g (98%).

EXAMPLE 4

Diethyl methylmalonate (1.74 g, 10 mmol), 1.38 g (10 mmol) of potassium carbonate, 0.12 g of tetra-n-butylammonium bromide, and 5 mL of carbon tetrachloride were mixed at 70° C. for 3 h. Gas chromatographic analysis of the mixture showed complete conversion of the diethyl methylmalonate to give 2.04 g of diethyl α-chloro-α-methylmalonate (98% yield).

EXAMPLE 5

Phenylacetylene (1.02 g, 10 mmol), 1.92 g of cesium carbonate (10 mmol), and 0.15 g tetra-n-butylammonium chloride hydrate and 5 mL carbon tetrachloride were mixed at 70° C. for 5 h. Gas chromatographic analysis of the mixture showed that it contained 1.32 g of 1-chloro-2-phenylacetylene (96% yield).

EXAMPLE 6

Ethyl 2-acetylbutyrate (1.58 g, 10 mmol), 1.38 g potassium carbonate (10mmol), 0.2 g of tetra-n-butylammonium chloride hydrate, and 5 mL bromotrigraphic analysis of the resulting mixture showed the presence of 1.56 g of ethyl 2-acetyl-2-bromobutyrate (65% yield).

EXAMPLE 7

Dimethyl methylmalonate (1.46 g, 10 mmol), 1.38 g (10 mmol) potassium carbonate, 0.1 g of tetra-n-butylammonium hydrogen sulphate, and 5 mL of carbon tetrachloride were mixed at 70° C. for 4 h. Complete conversion of dimethyl methylmalonate was determined by gas chromatography. Yield of dimethyl α-chloro-α-methylmalonate was 1.73 g (96%).

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

I claim:

1. A process for halogenating an organic carbon acid compound containing both a single acidic hydrogen atom and at least one electron withdrawing group attached to the same carbon atom, comprising the step of: reacting said carbon acid compound in solution with a halogenating agent selected from the group consisting of perhalomethanes wherein the halogen substituents are I, Br, Cl or mixtures thereof, trihaloacetic acid esters wherein the halogen substituents are Br, Cl or mixtures thereof, and perfluoroalkyl halides wherein the halide is I, Br, Cl or mixtures thereof, in the presence of (i) a phase transfer catalyst of the formula $R^1R^2R^3R^4LJ$ where L is selected from the group consisting of phosphorous and nitrogen, where J is an inorganic anion other than fluoride, and where $R^1$, $R^2$, $R^3$ and $R^4$ are independently chosen from the group consisting of hydrocarbyl radicals containing from 1 to about 20 carbon atoms and (ii) a mild inorganic base which is insoluble in the reaction medium, to provide a halogenated product wherein said single acidic hydrogen atom of the carbon acid compound is replaced with a halogen selected from the group consisting of chlorine, bromine and iodine.

2. The process of claim 1 wherein the halogenation reaction is run at a temperature between 0° C. and 150° C.

3. The process of claim 2 wherein the carbon acid compound is a compound of the formula $R^5-C\equiv C-H$ wherein $R^5$ is a hydrocarbyl group containing between 1 and about 10 carbon atoms.

4. The process of claim 3 wherein the carbon acid compound is phenylacetylene.

5. The process of claim 3 wherein the base is $Cs_2CO_3$.

6. The process of claim 2 wherein the carbon acid compound is a compound of the formula HCXYZ wherein X is an electron withdrawing group, Y is an electron withdrawing group or an aromatic group which is unsubstituted or substituted with a group which is inert under reaction conditions, and Z is an electron withdrawing group, an aromatic group which is unsubstituted or substituted with a group which is inert under reaction conditions, or a linear or branched, saturated or unsaturated alkyl group which is unsubstituted or substituted with a group which is inert under reaction conditions.

7. The process of claim 6 wherein the electron withdrawing group is a nitrile, an aldehyde group, a ketone group of the formula $-C(=O)-R^6$ or an ester group of the formula $-C(=O)-OR^6$ where $R^6$ is a hydrocarbyl group.

8. The process of claim 6 wherein X is $-COOCH_3$, $-COOC_2H_5$, $-COCH_3$ or $-CN$; wherein Y is $-COOCH_3$, $-COOC_2H_5$ or $-COCH_3$; and wherein Z is $-CH_3$, $-C_2H_5$ or $-C_6H_5$.

9. The process of claim 2 wherein the carbon acid compound is a trihalomethane.

10. The process of claim 2 wherein the halogenating agent is a perhalomethane.

11. The process of claim 10 wherein the carbon acid compound is chlorinated and the halogenating agent is $CCl_4$.

12. The process of claim 10 wherein the carbon acid compound is brominated and the halogenating agent is $CBrCl_3$.

13. The process of claim 2 wherein the halogenating agent is a trihaloacetic acid.

14. The process of claim 2 wherein the halogenating agent is a perfluoroalkyl halide.

15. The process of claim 14 wherein the carbon acid compound is iodinated and the halogenating agent is perfluoro-n-hexyl iodide.

16. The process of claim 2 wherein the reaction medium consists essentially of the halogenating agent.

17. The process of claim 2 wherein the inorganic base is selected from $Na_2CO_3$, $K_2CO_3$, $Cs_2CO_3$, $NaHCO_3$ and KF.

18. The process of claim 2 wherein $R^1$, $R^2$, $R^3$ and $R^4$ are aliphatic groups containing from 1 to about 10 carbon atoms.

19. The process of claim 2 wherein $R^1$, $R^2$, $R^3$ and $R^4$ are alkyl groups.

20. The process of claim 2 wherein $R^1$, $R^2$, $R^3$ and $R^4$ are selected from n-butyl, n-hexyl and n-octyl.

21. The process of claim 2 wherein $R^1$, $R^2$, $R^3$ and $R^4$ are n-butyl.

22. The process of claim 2 wherein L is phosphorus.

23. The process of claim 2 wherein L is nitrogen.

24. The process of claim 2 wherein J is selected from the group consisting of $Cl^-$, $Br^-$, $I^-$, $HSO_4^-$ and $NO_3^-$.

* * * * *